US006623775B2

(12) United States Patent
Johnson et al.

(10) Patent No.: US 6,623,775 B2
(45) Date of Patent: *Sep. 23, 2003

(54) TREATING OR PREVENTING ILLNESS GROWTH OF *CLOSTRIDIUM DIFFICILE*

(75) Inventors: Eric A. Johnson, Madison, WI (US); Gerhard J. Haas, Woodcliff Lake, NJ (US)

(73) Assignee: S.S. Steiner, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/809,146

(22) Filed: Mar. 15, 2001

(65) Prior Publication Data

US 2001/0014365 A1 Aug. 16, 2001

Related U.S. Application Data

(62) Division of application No. 08/949,258, filed on Oct. 10, 1997, now Pat. No. 6,251,461.

(51) Int. Cl.[7] .......................... A23L 3/3508; C12Q 1/18; C12Q 1/02; C12N 1/06
(52) U.S. Cl. ....................... 426/335; 426/532; 426/600; 424/725; 435/29; 435/32; 435/252.7; 435/842
(58) Field of Search ................... 424/9.1, 725; 426/335, 426/600, 532; 435/29, 32, 252.7, 842

(56) References Cited

U.S. PATENT DOCUMENTS 3,932,603 A * 1/1976 Haas ........................... 424/49
5,286,506 A * 2/1994 Millis et al. ................ 426/335

FOREIGN PATENT DOCUMENTS

| DE | 2749274 | 11/1976 |
| EP | 0606599 | 7/1994 |
| EP | 0 606 599 | * 7/1994 |
| EP | 0681029 | 11/1995 |

OTHER PUBLICATIONS

Haas et al. Antimicrobial Activity of Hop Resins. Journal of Food Protection. Jan. 1994. vol. 57, No. 1, pp. 59–61.*
Larson et al., "Antimicrobial activity of hop extracts against Listeria monocytogenes in media and in food", International Journal of Food Microbiology, 1996, 33,pp. 195–207.*
Ohsugi et al., "Antibacterial activity of Humulus lupulus against *Helicobacter pylori*", Journal of Traditional Medicines, 1996, vol. 13, No. 4, pp. 344–345.*
Ohsugi et al., "Antibacterial activity of traditional medecines and an active constituent lupulone from Humulus lupulus against *Helicobacter pylori*", Journal of Traditional Medicines, 1997, vol. 14, No. 3, pp. 186–191.*
Fernandez et al; "Aspects of the resistance of lactic acid bacteria to hop bitter acids"; 1993; pp. 315–319; Journal of Applied Bacteriology.
Smith et al; "Antibacterial Activity of Hop Bitter Resins Derived From Recovered Hopped Wort"; Feb. 1993; pp. 43–48; Journal of the Institute of Brewing, vol. 99.
Simpson; "Studies on the Sensitivity of Lactic Acid Bacteria to Hop Bitter Acids"; Sep.–Oct. 1993; Journal of the Institute of Brewing; vol. 99; pp. 405–411.
Simpson et al; "Factors affecting antibacterial activity of hop compounds and their derivatives"; 1992; pp. 327–334; Journal of Applied Bacteriology.
Mizobuchi et al; "Antifungal Activities of Hop Bitter Resins and Related Compounds"; 1985; pp. 399–403; Agric. Biol. Chem. 49(2).
Author unknown; title unknown; date unknown; pp. 1–2, 24–27; Final Report—Contact No. N43–AI–45215—publication unknown.

* cited by examiner

*Primary Examiner*—Sandra E. Saucier
*Assistant Examiner*—Vera Afremova
(74) *Attorney, Agent, or Firm*—Hayes Soloway P.C.

(57) ABSTRACT

The present invention relates to the discovery that hop extract is useful as an antibacterial agent against the dangerous pathogens *Clostridium botulinum*, *Clostridium difficile*, and *Helicobacter pylori* at levels below that at which a flavor from the acids contained therein is objectionable. More specifically, a process and associated product is described herein, comprising applying a solution of hop extract to a food, beverage or other medium so that the final concentration of hop ingredients is about 1 ppm or higher in order to inhibit the growth of *Clostridium botulinum*, *Clostridium difficile*, and/or *Helicobacter pylori*.

6 Claims, 15 Drawing Sheets

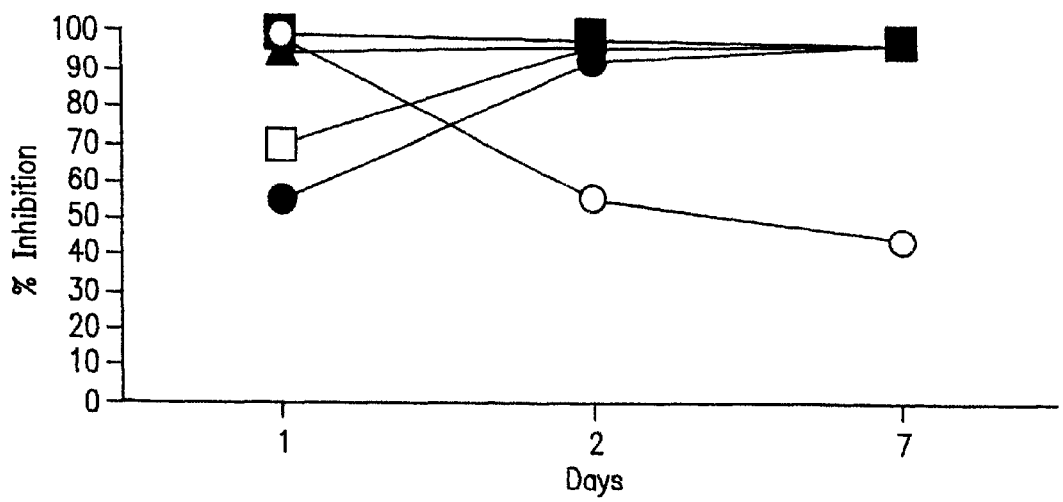
FIG. IA
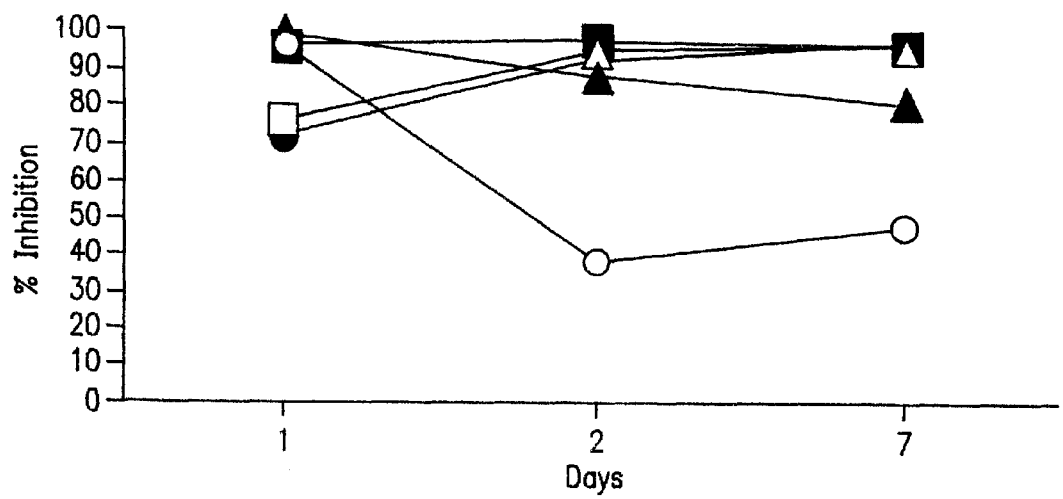
FIG. IB

- ─○─ 50% ETOH
- ─▲─ 1 ppm
- ─△─ 5 ppm
- ─■─ 10 ppm
- ─□─ 50 ppm
- ─●─ 100 ppm

- ─○─ 50% ETOH
- ─▲─ 1 ppm
- ─△─ 5 ppm
- ─■─ 10 ppm
- ─□─ 50 ppm
- ─●─ 100 ppm

─○─ 50% ETOH  ─▲─ 1 ppm  ─△─ 5 ppm
─■─ 10 ppm  ─□─ 50 ppm  ─●─ 100 ppm

─○─ 50% ETOH  ─▲─ 1 ppm  ─△─ 5 ppm
─■─ 10 ppm  ─□─ 50 ppm  ─●─ 100 ppm

——○—— 50% ETOH          ——▲—— 1 ppm          ——△—— 5 ppm
——■—— 10 ppm             ——□—— 50 ppm         ——●—— 100 ppm ——○—— 50% ETOH          ——▲—— 1 ppm          ——△—— 5 ppm
——■—— 10 ppm             ——□—— 50 ppm         ——●—— 100 ppm

TREATING OR PREVENTING ILLNESS GROWTH OF *CLOSTRIDIUM DIFFICILE*

CROSS-REFERENCE TO RELATED APPLICATION

This Application is a Divisional of U.S. application Ser. No. 08/949,258, filed Oct. 10, 1997, now U.S. Pat. No. 6,251,461, issued Jun. 26, 2001.

FIELD OF THE INVENTION

The present invention relates to the use of hop extracts for controlling *Clostridium botulinum, Clostridium difficile*, and *Helicobacter pylori*.

BACKGROUND OF THE INVENTION

The most prevalent groups of bitter acids found as components of hops are the alpha-acids and beta-acids, also referred to as humulones and lupulones, respectively. Both contribute bitterness to beer, but the alpha-acids are much more intense in this regard than the beta-acids. Producers of hop extracts have recently used liquid carbon dioxide under supercritical conditions. A by-product of the operation is a product which contains approximately 61 weight percent beta-acids, the remainder consisting essentially of other hop resins.

Quite apart from their use in beer, hops and hop acids have also been recognized as microbial inhibitors. More specifically, hop acids and resins have been shown to be primarily active against some gram positive bacteria and Mycobacteria. Activity against gram negative bacteria is far less pronounced. It has been suggested that the reduced effect was due to induced permeability of the cell membrane in gram positive bacteria, but was inactivated by the serum phosphatides in gram negative bacteria Arch. Mikrobiol. 94, pp. 159–171, 1973.

Other more recent references have been identified, such as U.S. Pat. No. 5,286,506 (1994) and Larson, Yu, Price, Haas and Johnson, *International Journal of Food Microbiology*, 1996, which report on the use of beta acids as extracted from hops for controlling Listeria. More specifically, 6 to 50 ppm of beta acids, as extracted from hops, was found in media to protect against *Listeria monocytogenes* contamination, while in foods, depending on the specific food, higher levels (100–300 ppm) were necessary.

Attention is also directed to the following references: *Agricultural and Biological Chemistry*, Vol. 49, No. 2, pp 399–404 (1985) which discloses that humulone, lupulone and related compounds were found to have antifungal activities; *Dissertation Abstracts*, Vol. 53–08B, 1991, pp. 38–61, reports that compounds derived from hops possess antibacterial activity, and more specifically, the antibacterial activity against *Lactobacillus brevis* was found to be pH-dependent; *Journal of the Institute of Brewing*. 99 (5) 405–411 (1993) reports on the results of studies investigating the ability of hop acids to inhibit beer spoilage activity; *Journal of the Institute of Brewing*, 99 (1) 43–48 (1993) reports on the antibacterial activity of hop bitter resins derived from recovered hopped worts. More specifically, strains of thermophilic *Bacillus spp*) were identified which failed to grow in certain sweet worts derived from mashes to which centrate (recovered hop wort) had been added; *J. Food Prot*. Vol 57, No. 1, pp 59–61 (1994) reports on the antimicrobial activity of hop resins against *Streptococcus salivarius*. The two hop resins used were iso-alpha acid and beta resin; *Agric. Biol. Chem.*, Vol. 49, No. 2, pp. 399–403 (1985) disc that humulone, lupulone and related compounds as having antifungal activities; *Lebensm. Ind*. Vol. 28, No. 7, pp. 311–315 (1981) reports that tests showed that hop extract and isomerized hop extract have similar anti-microbial properties like hops, but the antimicrobial effect of the hops in beer production was low. *J. Appl. Bacteriol.*, Vol. 72, No. 4, pp. 327–324 (1992) cons the antibacterial effect of weak acids derived from the hop plant *Humulus lupulus*. The antibacterial activity of trans-isohumulone was about 20 times greater than that of humulone, 11 times greater than colupulone, and nine times greater than that of trans-humulinic acid when the degree of ionization was taken into account.

However not all gram positive bacteria are sensitive to hop resins as is well known to the Brewer and see J. Fernandez and Will Simpson in J. App Bacteriology, 75 315–319 (1993). Also G. Haas and B. Barsoumian in J. Food Protection 57, 59–61 (1994) worked with a strain of *Bacillus subtilis* which was resistant.

None of the art noted above deals with the control of botulism, which is well-known as an acute intoxication manifested by neuromuscular disturbances after ingesting food containing a toxin elaborated by *Clostridium botulinum*. The causative agent is actually one of several types of exotoxins elaborated by the sporulating, anaerobic bacillus *Clostridium botulinum*, which causes human poisoning. *Botulinum* toxins are highly poisonous proteins resistant to digestion by gastrointestinal enzymes. *Clostridium difficile* is one of the major causes of diarrheal disease particularly in elderly humans treated with antibiotics. Very few antibiotics are effective and treatment of this infection is difficult at best. Only vancomycin of the well known antibiotics seems to be useful in treatment. *Helicobacter pylori* is a common cause of gastric ulcers and chronic active gastritis in humans. Ulcer relapses are common in humans treated with antibiotics or bismith nitrate. Other intervention strategies have to be sought and a nutritional or dietetic approach would be highly desirable.

SUMMARY OF INVENTION

The present invention relates to the discovery that hops extract or the components of hops extract are useful as an antibacterial agent against dangerous pathogens *Clostridium botulinum, Clostridium difficile*, and *Helicobacter pyroli*. More specifically, a process and associated product is described herein, comprising applying at least about 1 ppm or greater, by weight, of beta acids, or hop extracts to inhibit growth of *Clostridium botulinum, Clostridium difficile*, and *Helicobacter pylori*. Medications, disinfectant solutions or pharmaceutical compositions containing these materials may also be used.

BRIEF DESCRIPTION OF THE DRAWINGS

FIGS. 1A, 1B and 1C illustrate the inhibition of *Clostridium botulinum* 56A by hop extracts "a" (41% beta, 12% alpha and 47% desoxy alpha, hop oils and hop waxes), "b" (65% w/v beta acids) and "c" (6% w/v post beta-acids in Tween 80), at different concentrations in ethanol (50%) solution.

DETAILED DESCRIPTION

The present invention relates to the discovery that hop extracts or fractions are useful as a preservative inhibiting the pathogens *Clostridium botulinum, Clostridium difficile,* and *Helicobacter pylori* and as agents to prevent illness caused by said pathogens. Three different hop extracts were evaluated to demonstrate the broad applicability of the present invention.

The hop extracts as used herein may comprise solvent extracted hops, or liquid $CO_2$ or supercritical $CO_2$ gas extracted hops. Particularly preferred are $CO_2$ liquid or $CO_2$ critical gas extracts. Generally, the hop extracts are added to a food product or other vehicle, in solution, to achieve at least about one part per million, by weight, of beta acids in the GI tract or stomach. Amounts less than about 1 ppm, by weight, beta acids, does not appear to provide protection against *Clostridium botulinum* and *Clostridium difficile*. The solution preferably contains about 5 ppm–100 ppm, by weight, of beta acids. The upper level is dictated by taste and solubility.

Figure 1C:
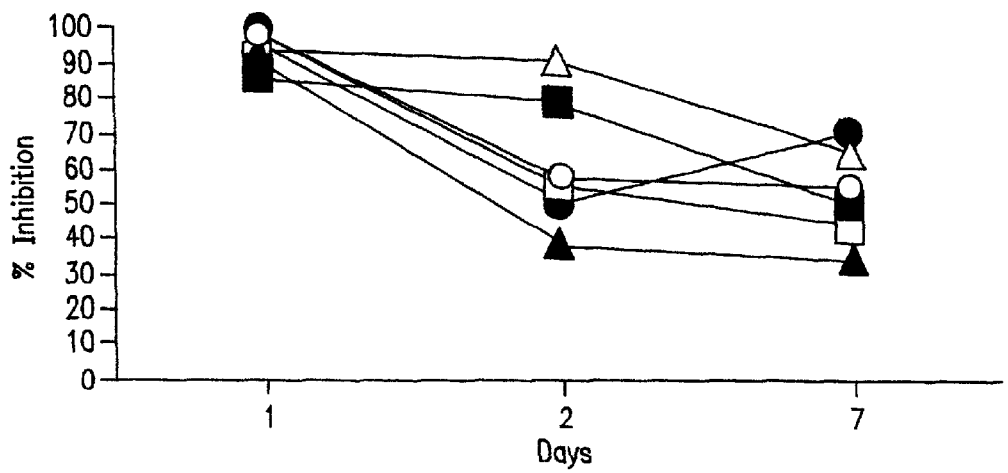
Figure 2A:
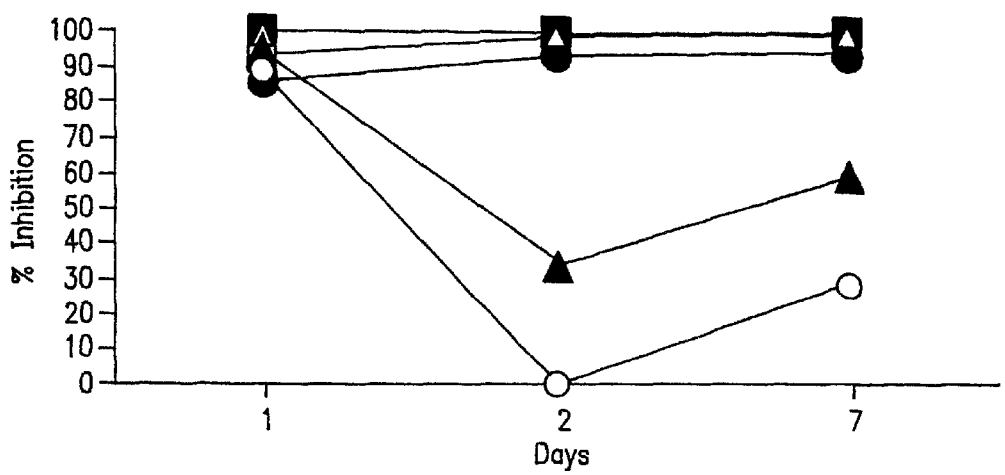
FIGS. 2A, 2B and 2C illustrate the inhibition of *Clostridium botulinum* 62A by hop extracts a, b and c, as described above.
Figure 2B:
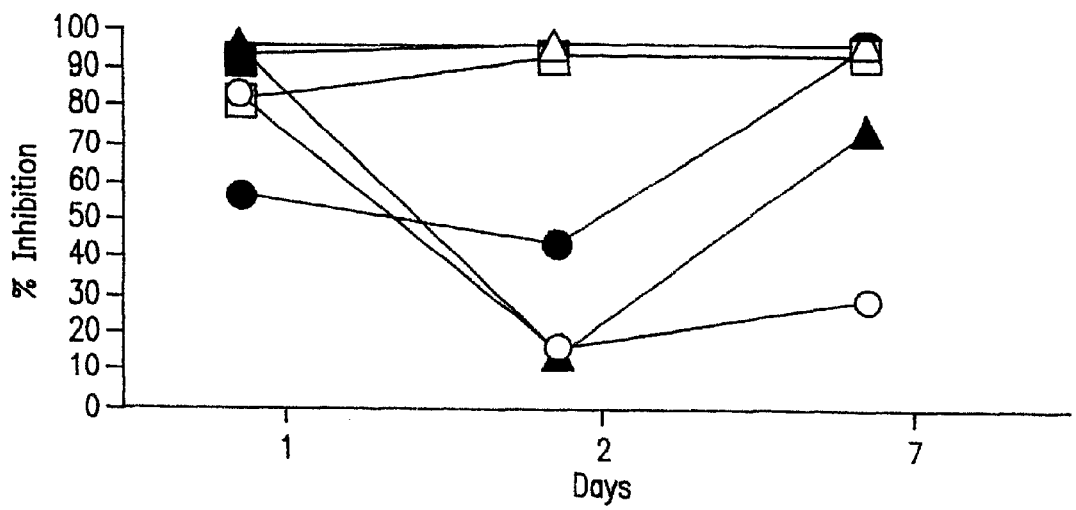
Figure 2C:
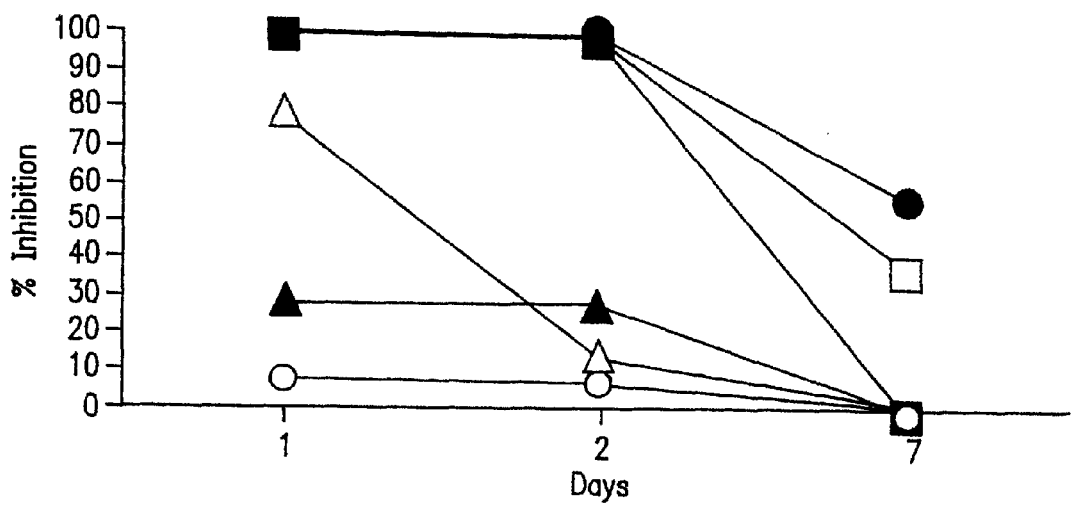
Figure 3A:
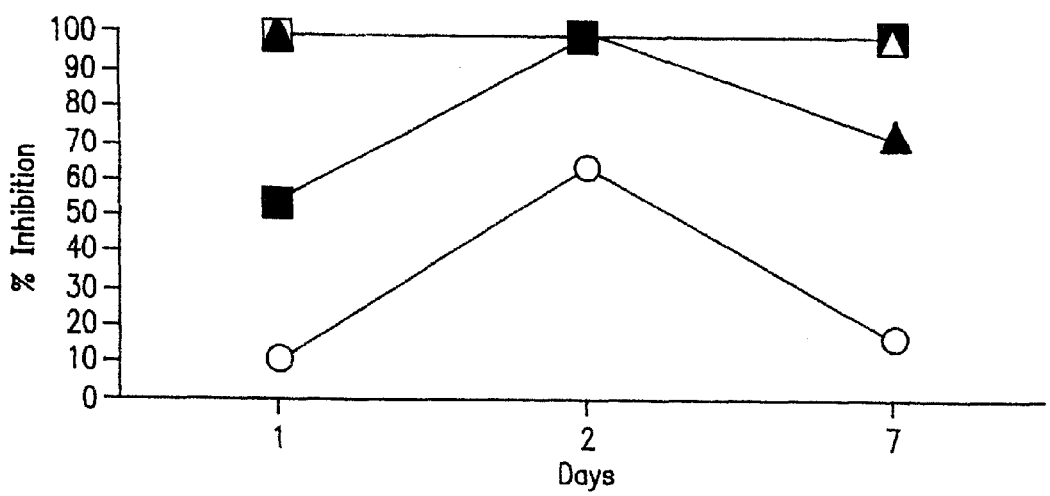
FIGS. 3A, 3B and 3C illustrate the inhibition of *Clostridium botulinum* 213B by hop extracts a, b and c, as described above.
Figure 3B:
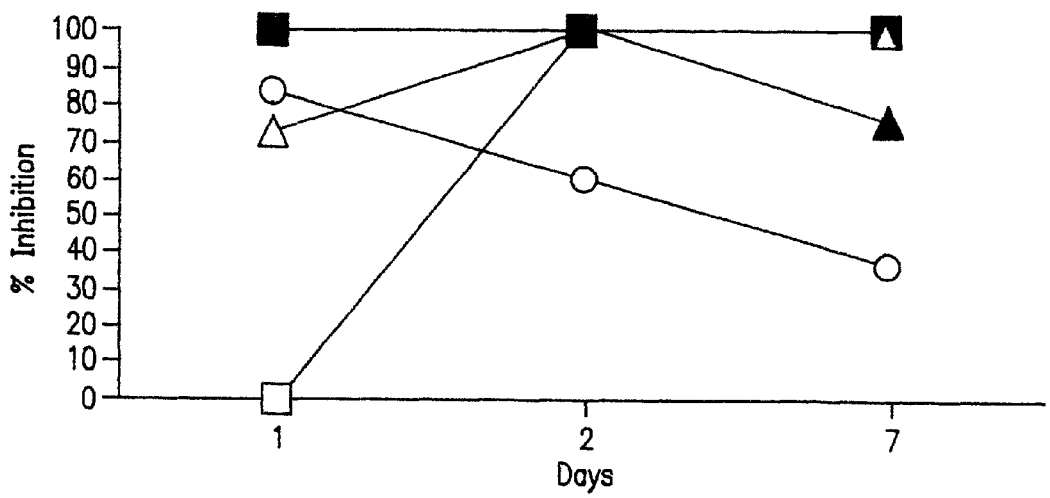
Figure 3C:
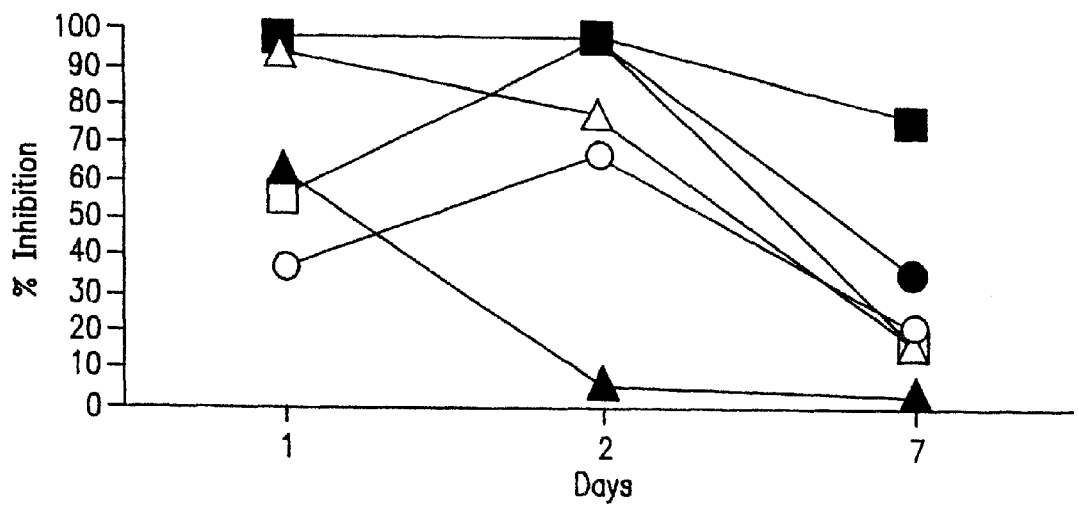
Figure 4A:
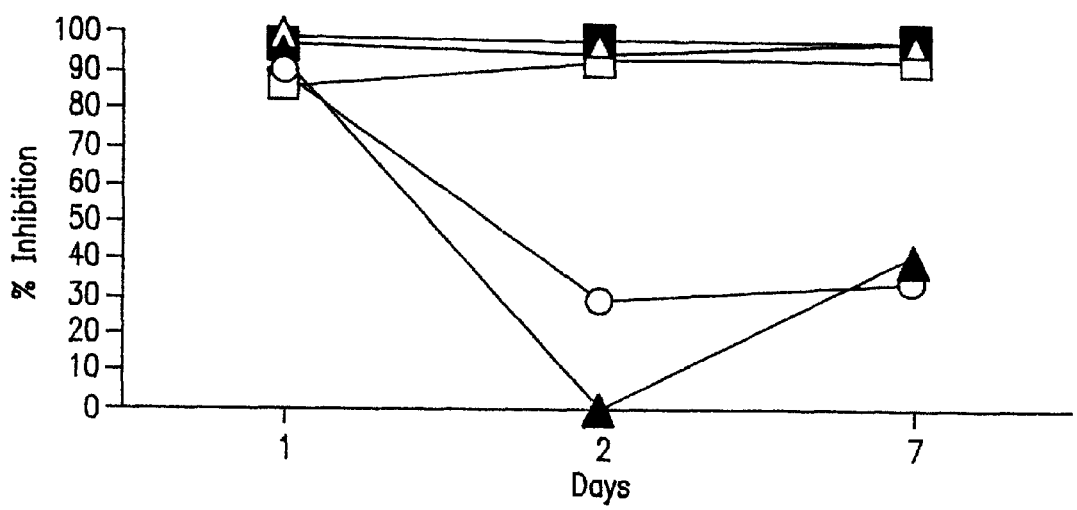
FIGS. 4A, 4B and 4C illustrate the inhibition of *Clostridium botulinum* Lamanna-Okra B by hop extracts a, b and c, as described above.
Figure 4B:
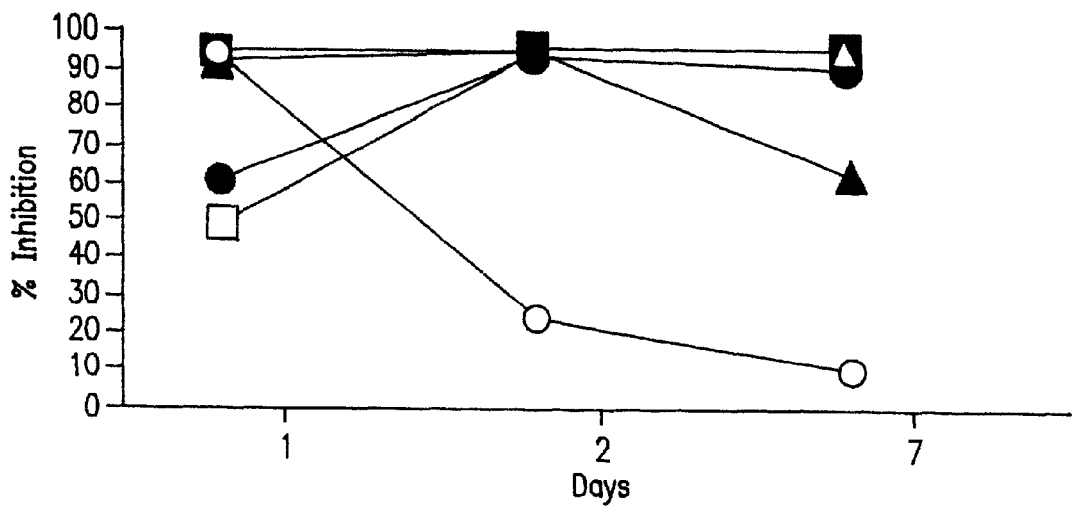
Figure 4C:
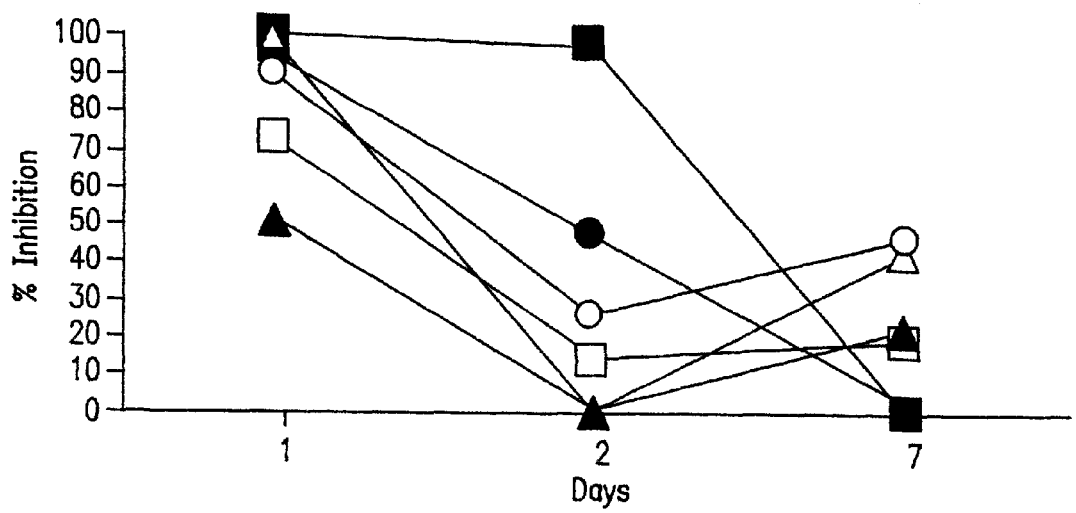
Figure 5A:
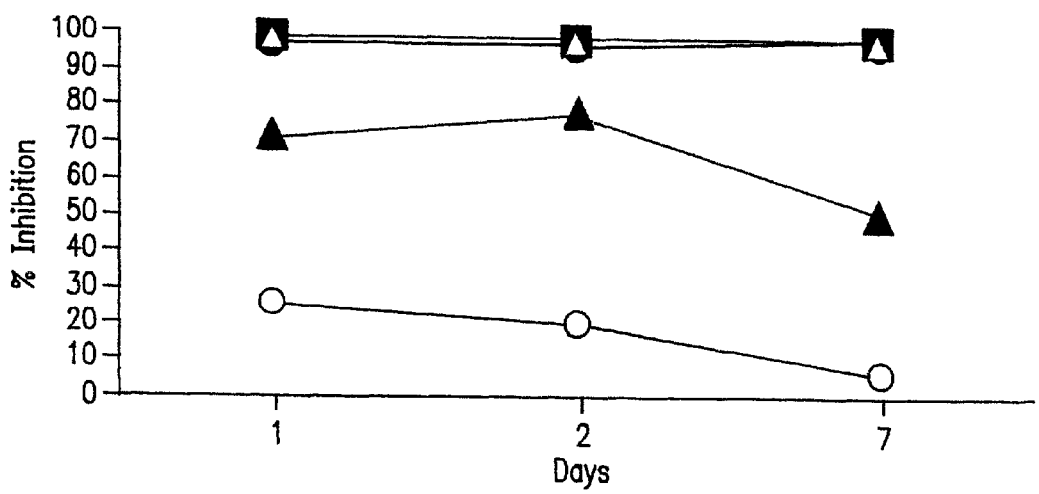
FIGS. 5A, 5B and 5C illustrate the inhibition of *Clostridium botulinum* Alaskan E by hop extracts a, b and c, as described above.
Figure 5B:
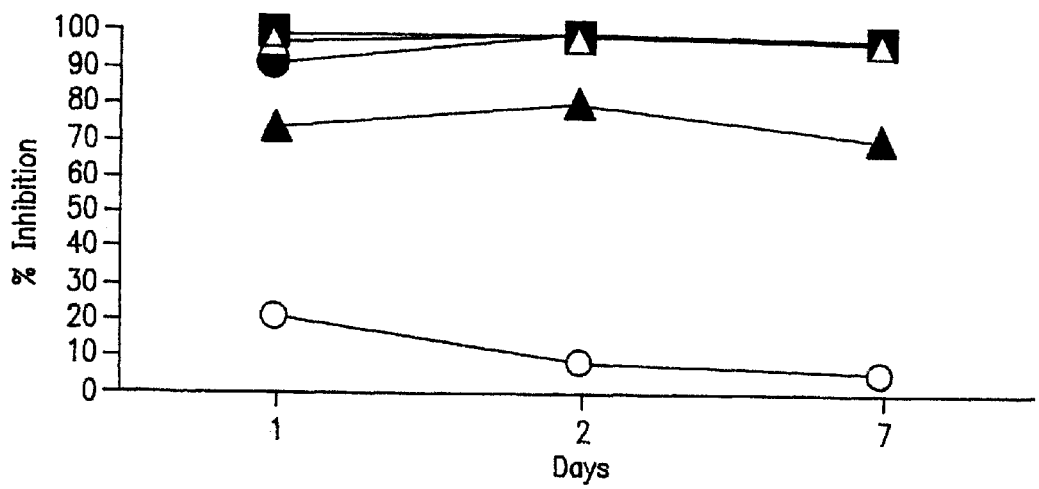
Figure 5C:
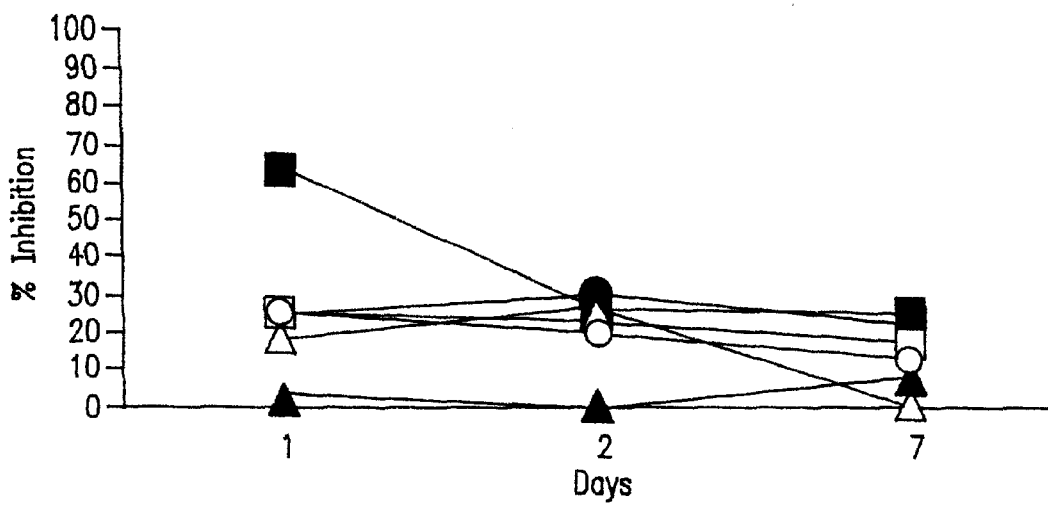
Figure 6A:
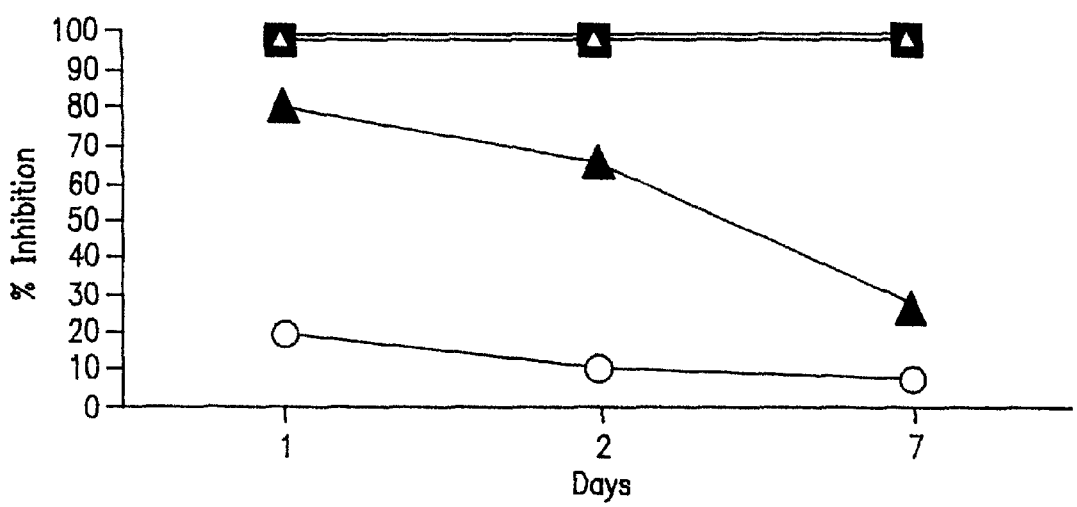
FIGS. 6A, 6B and 6C illustrate the inhibition of *Clostridium botulinum* Beluga E by hop extracts a, b and c, as described above.
Figure 6B:
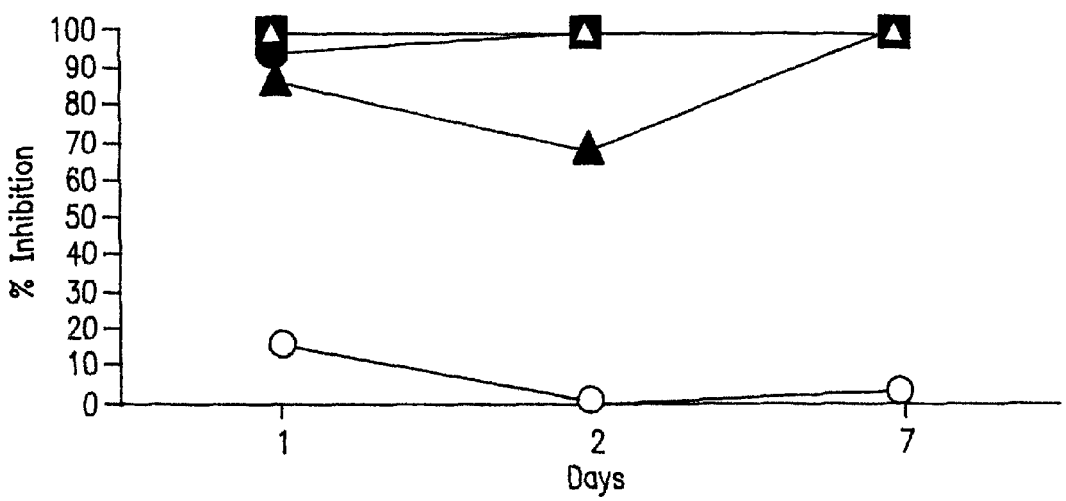
Figure 6C:
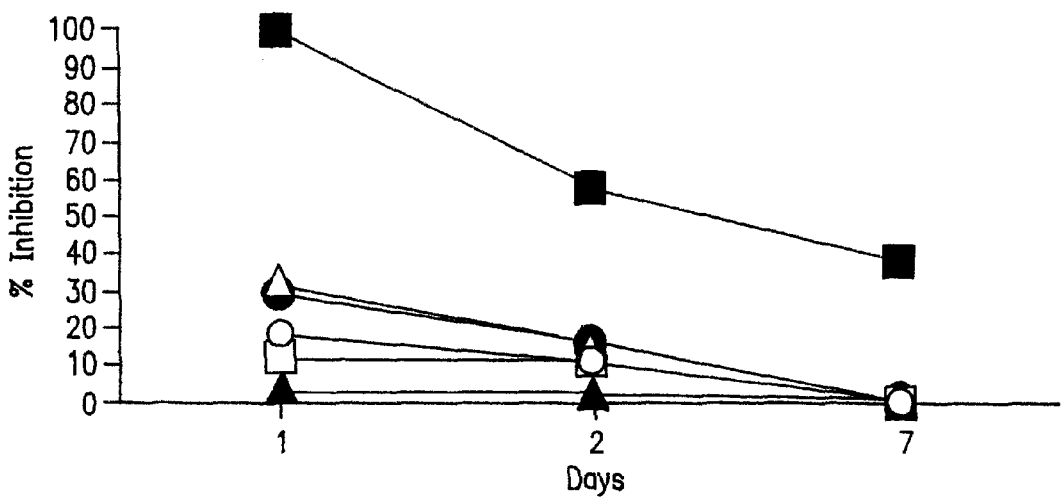
Figure 7A:
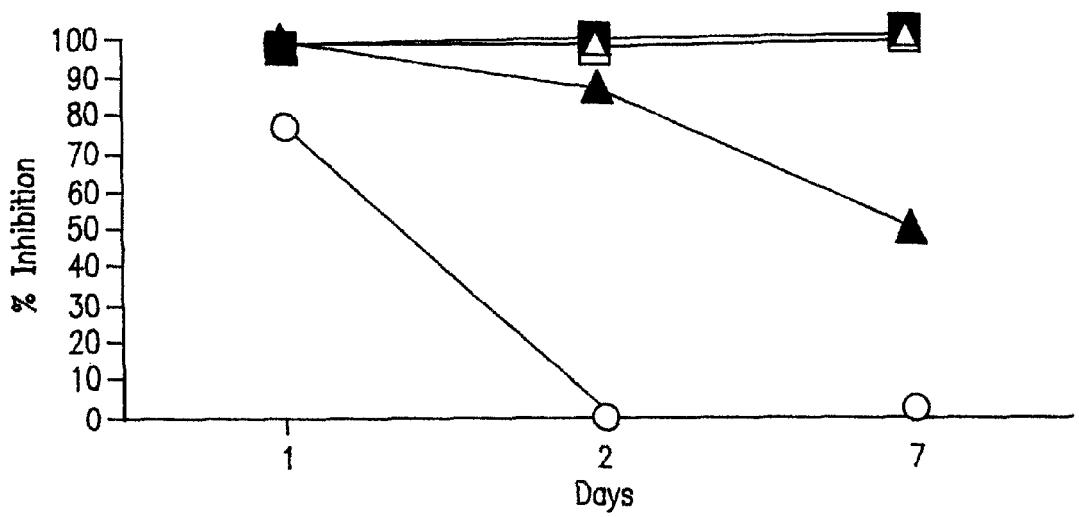
FIGS. 7A, 7B and 7C illustrate the inhibition of *Clostridium botulinum* 17 by hop extracts a, b and c, as described above.
Figure 7B:
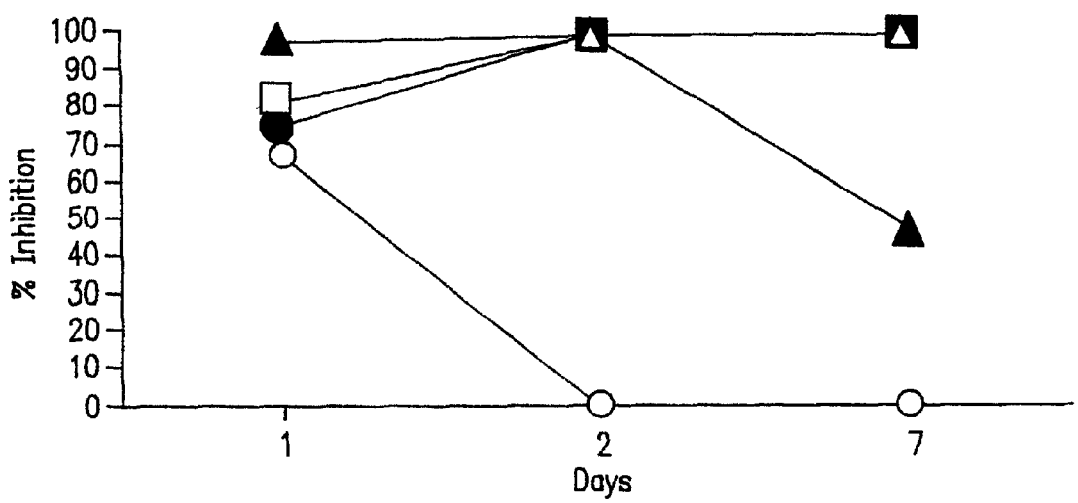
Figure 7C:
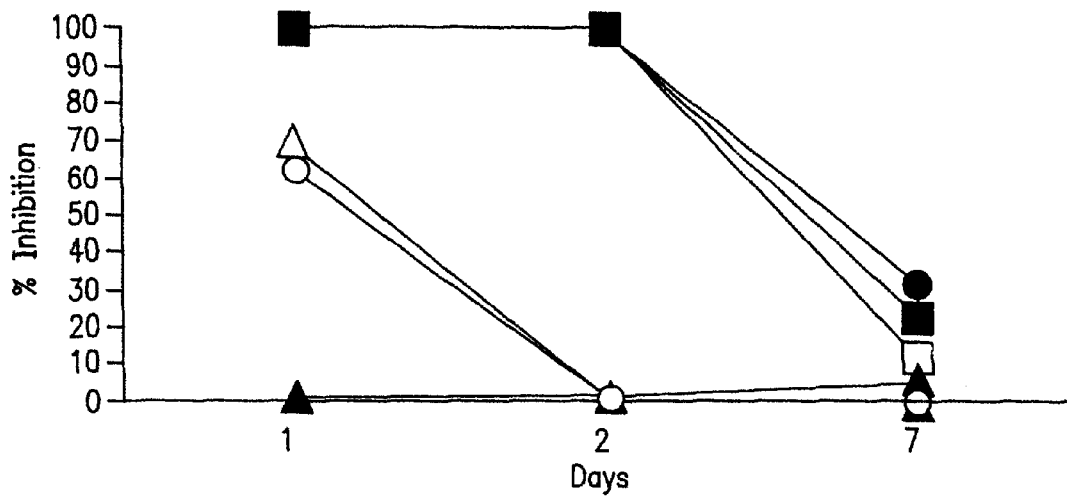
Figure 8A:
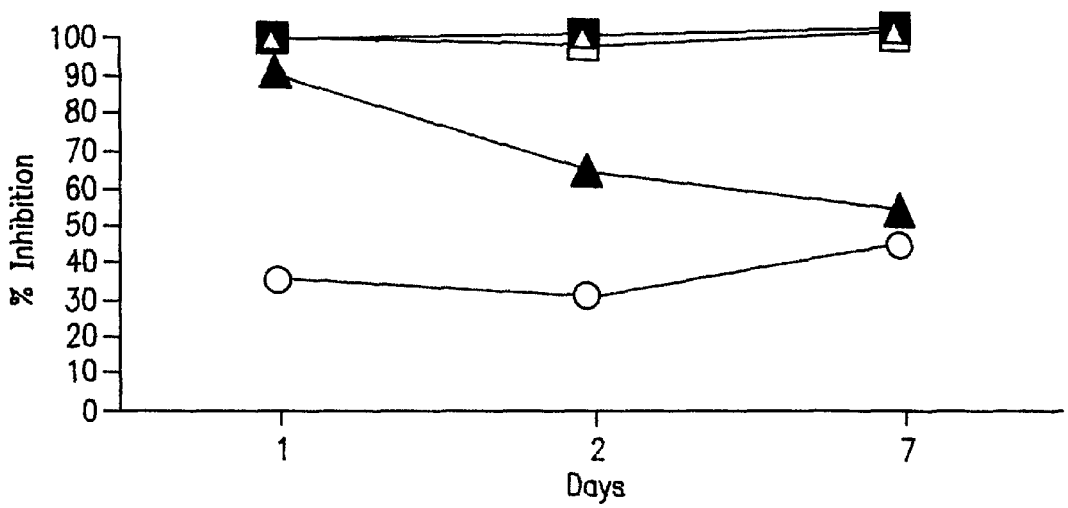
FIGS. 8A, 8B and 8C illustrate the inhibition of *Clostridium botulinum* 4848B by hop extracts a, b and c, as described above.
Figure 8B:
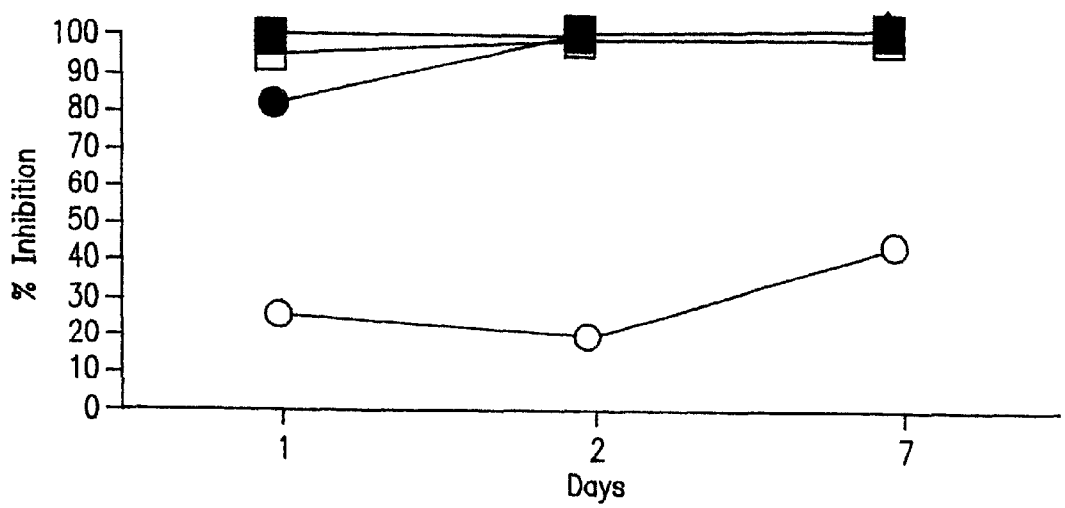
Figure 8C:
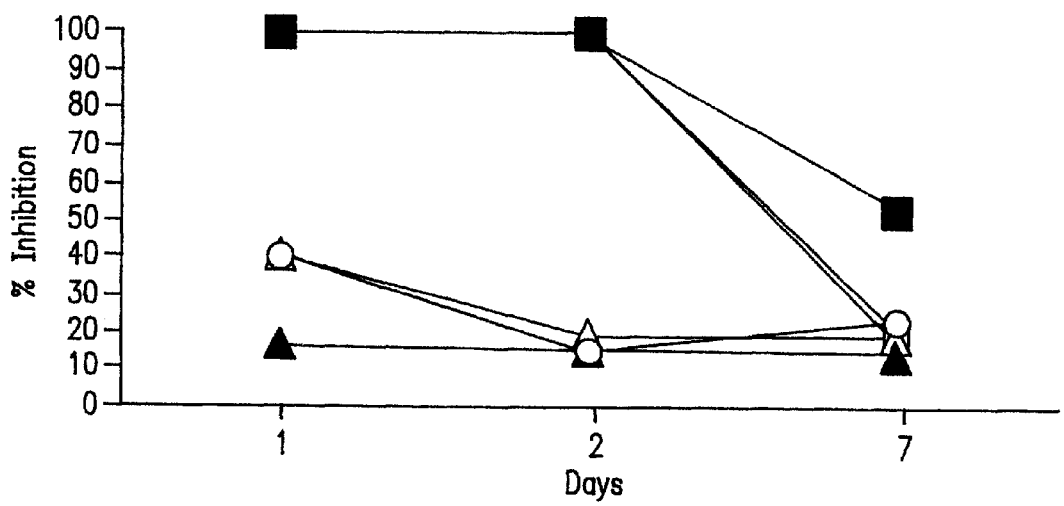
Figure 9A:
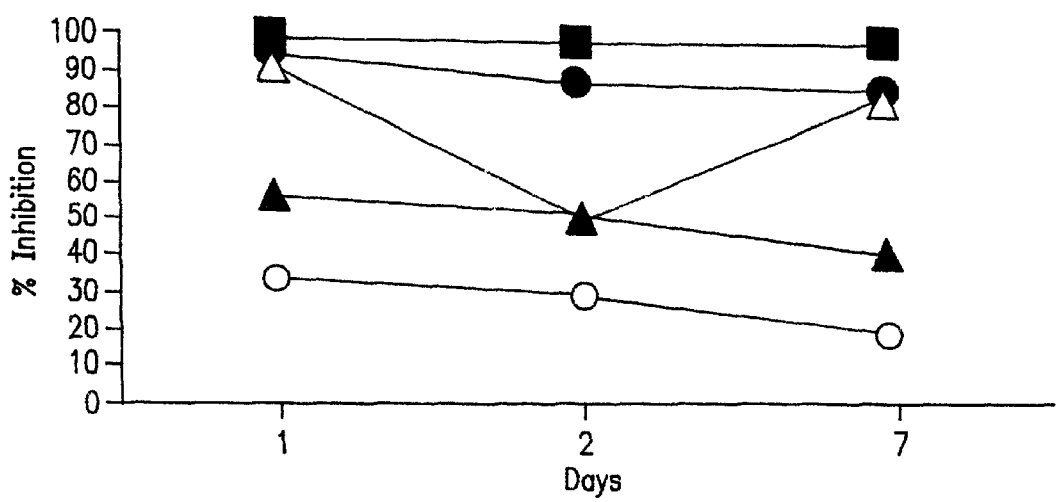
FIGS. 9A, 9B and 9C illustrate the inhibition of *Clostridium difficile* 43255 by hop extracts a, b and c, as described above.
Figure 9B:
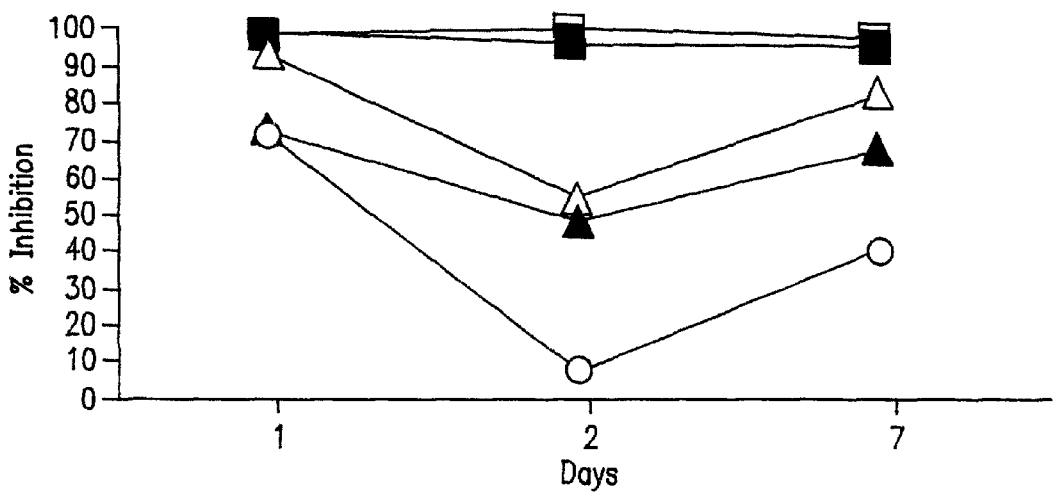
Figure 9C:
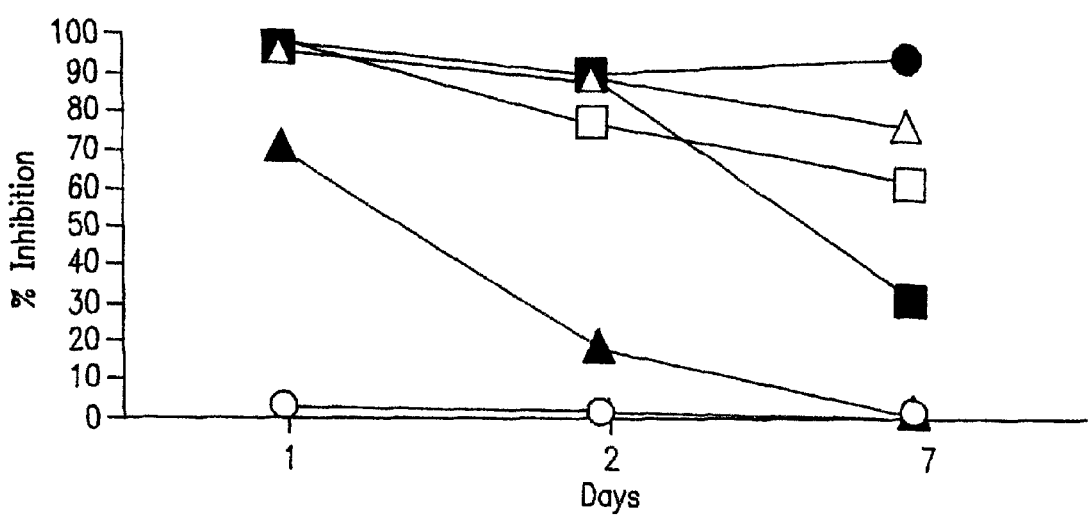
Figure 10A:
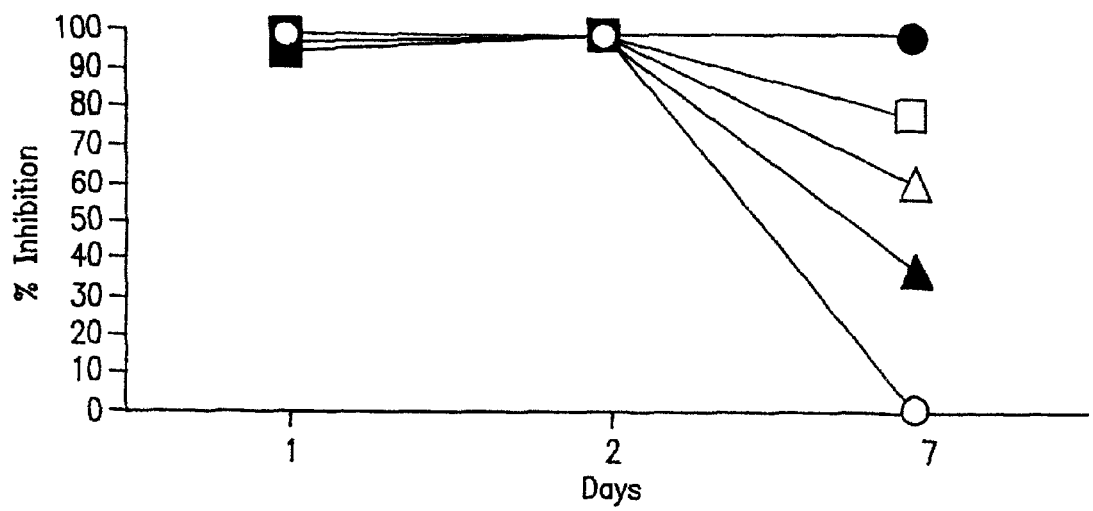
FIGS. 10A, 10B and 10C illustrate the inhibition of *Clostridium difficile* 10463 by hop extracts a, b and c, as described above.
Figure 10B:
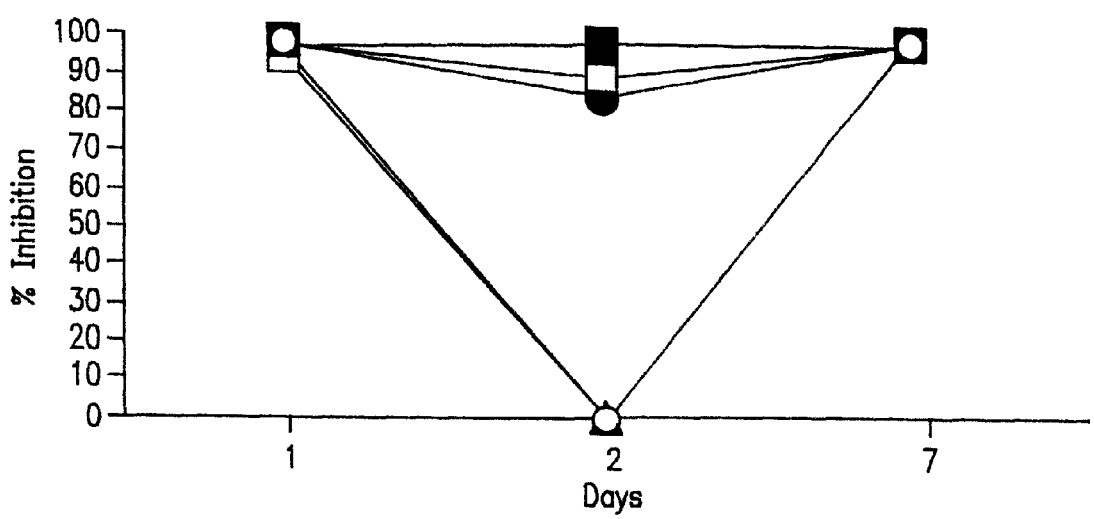
Figure 10C:
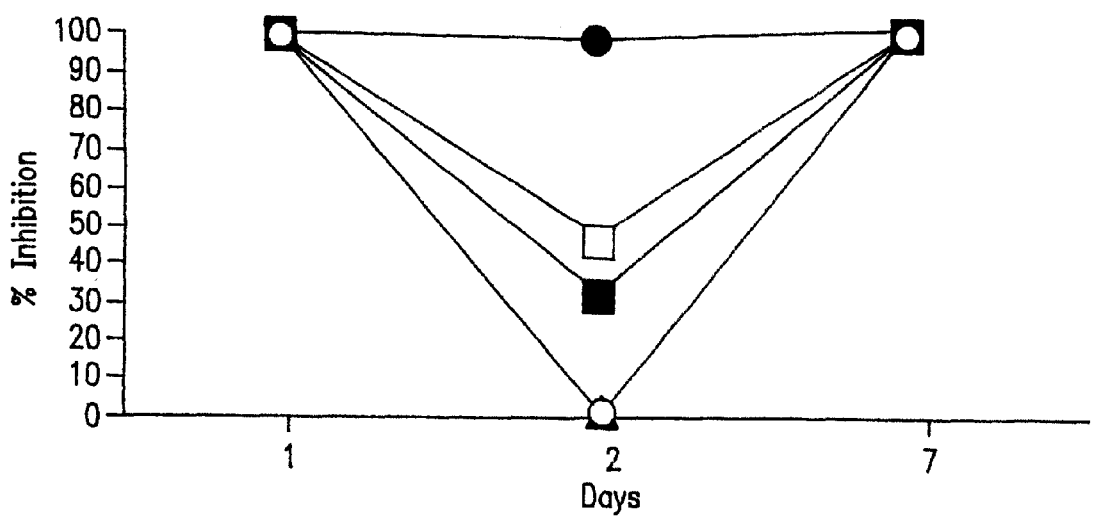

FIGS. 1–10 collectively illustrate the experimental results confirming the antimicrobial effects disclosed herein. More specifically, and as noted above in the brief description of the drawings, FIGS. 1A through 10A reference the use of hop extract "a", which contained 41% beta, 12% alpha and the remaining 47% contained a mixture of desoxy-alpha, hop oils and hop waxes. FIGS. 1B–10B refers to the use of hop extract "b", which contained 65% (w/v) beta acids. FIGS. 1C–10C refer to hop extract "c" which contained 6% (w/v) post beta acids in Tween 80. In each case the hop extract was made up as a solution in 50% ethanol, and added to achieve 1, 5, 10, 50 and 100 ppm. A control with 50% ethanol but without hop resin was included.

The organisms targeted in this invention included 8 strains of *Clostridium botulinum* and two strains of *Clostridium difficile*, as listed below:

| *Clostridium botulinum*: | |
| --- | --- |
| Proteolytic type A: | 56A, 62A |
| Proteolytic type B: | 213B, Lamanna-Okra B, |
| Non-proteolytic type B: | 17B, 4848B, |
| Non-proteolytic type E: | Alaska E, Beluga E |

*Clostridium difficile*

43255

10463

These organisms are toxicogenic and have been involved in human intoxication or infections.

The inhibition of *Clostridium botulinum* by hop extracts in broth media was established as follows:

Eight strains of *Clostridium botulinum* were inoculated as spores separately into tubes of 10 ml trypticase peptone-glucose-yeast extract (TPGY) broth containing 5 different levels (1, 5, 10, 50 and 100 ppm) of three hop extracts. Before inoculation, spores were treated with a heat treatment to activate them in order to achieve maximum germination. For proteolytic strains, spores were heat treated at 80° C. for 10 min and spores from non-proteolytic strains were treated at 60° C. for 20 min. Dilutions were made to have an initial inoculum ranging between $2\times10^3$ and $3\times10^3$ spores/ml.

*Clostridium difficile* strains were incubated in Brain Heart Infusion (BHI), 0.1% Yeast Extract (UYE) broth at 37° C.

As noted, hop extracts "a", "b" and "c" were tested at five different concentrations in the final medium: 1, 5, 10, 50, and 100 ppm. The tubes were incubated at 30° C. for one week. Growth (measured as increased absorbance) was monitored by optical density (O.D. at 660 nm) at one, two and seven days. Controls (only broth) and ethanol controls were inoculated with the spores but hop extracts were not added. All combinations of variables were tested in duplicate and replicated at least once.

With attention now directed at FIGS. 1A, 1B and 1C through 10A, 10B and 10C, as illustrated therein, hop extracts "a" and "b" produced inhibitory activity towards all eight *Clostridium botulinum* strains at a concentration as low as 1 ppm, and more preferably at concentrations of 5, 10, 50 and 100 ppm. Accordingly, 5–100 ppm of hop extracts "a" and "b" were found as the most preferred in the broad context of the present invention as applied to the *Clostridium botulinum* strain. Similarly, spores of *Clostridium difficile* strains were inhibited by hop extracts "a", "b" and "c" also at concentrations as low as 1 ppm, and more preferably at concentrations of 5, 10, 50 and 100 ppm, establishing effectiveness at the similar preferred range of 5–100 ppm.

The results above confirm that with regards to *botulinum*, hop extracts, quite apart from the known use in beer, have proven to be uniquely suited to provide effective inhibitory activity against this very important food pathogen. In addition, hop extracts also have shown their inhibitory activity against *Clostridium difficile* strains. The hop extracts therefore may be conveniently incorporated into a food product by dipping or spraying the food product with a solution of the extracts or alternatively added to a suitable vehicle such as an oral formulation to treat or prevent disease caused by the above microbes.

The following experimental procedure was applied with respect to confirmation of the inhibition of growth of *Helicobacter pylori* by hop extracts in broth media: Hop extracts "a" and "b" were dissolved in 95% EtOH, filter sterilized through a 0.45 μm syringe filter, and further diluted in filter sterilized 95% EtOH. Ten ml tubes of trypticase soy broth were prepared by adding 0.1 ml of the appropriate dilution of hop extract per 10 ml tube to obtain final concentrations of 1, 5, 10 or 100 ppm hop extract. Controls were prepared by adding 0.1 ml of filter sterilized $dH_2O$ per 10 ml tube. Ethanol controls were also prepared by adding 0.1 ml filter sterilized 95% EtOH per tube.

An 18 hour overnight culture of *Helicobacter pylori* (ATCC 43504) in tryptic soy broth (TSB) was inoculated (0.1 ml per 10 ml TSB) into prepared TSB tubes. Caps were loosened on tubes, which were incubated at 37° C. in anaerobe jars containing BBL CampyPak Plus packets, which created a microaerophilic system in the jars. Growth was checked by monitoring optical density at 660 nm every day for 3 days. Initial inoculum level ($3.8 \times 10^5$ CFU/ml) was determined by diluting inoculum in 67 mM sodium phosphate buffer and pour plating onto Plate Count Agar, which was incubated 24 hours at 37° C. The results are provided below in Table I:

TABLE I

RESULTS

|  | Day 1 | Day 2 | Day 3 |
|---|---|---|---|
| control (0 ppm) | G | G | G |
| EtOH control | G | G | G |
| 1 ppm HE#2 | NG | NG | NG |
| 5 ppm HE#2 | NG | NG | NG |
| 10 ppm HE#2 | NG | NG | NG |
| 100 ppm HE#2 | NG | NG | NG |
| 1 ppm HE#3 | G | G | G |
| 5 ppm HE#3 | NG | NG | NG |
| 10 ppm HE#3 | NG | NG | NG |
| 100 ppm HE#3 | NG | NG | NG |

G = growth
NG = no growth

Conclusion

Growth of *H. pylori* was completely inhibited in TSG at 37° C. over 3 days by hop extract #2 at levels as low as 1 ppm, and by hop extract #3 levels as low as 5 ppm.

As can be seen from the above, growth of *Helicobacter pylori* was completely inhibited in TSB at 37° C. over 3 days by hop extract "a" at levels as low as 1 ppm, and by hop extract "b" at levels as low as 5 ppm.

In addition to the above, those skilled in the art will recognize herein that the present invention also relates to the preparation of disinfectant compositions to inhibit growth, and pharmaceutical compositions to prevent transmission, of the pathogens identified herein, wherein said compositions comprise at least 1 ppm of hop extracts, or more preferably, 5, 10, 50 and 100 ppm, and/or the specific range between about 5–100 ppm.

I claim:

1. A method for treating a food or beverage containing *Clostridium difficile* so as to inhibit *Clostridium difficile* infection after the food or beverage is ingested, which method comprises treating the food or beverage with a solution containing a hop extract which is a solvent or a $CO_2$ extract containing at least 1 ppm by weight of beta-acids, whereby the growth of *Clostridium difficile* is inhibited.

2. The method of claim 1, wherein solution comprises an ethanolic solution.

3. The method of claim 1, wherein said solution contains 5–100 ppm, by weight, beta-acids.

4. The method of claim 1, wherein said extract comprises a mixture of (1) beta-acids, and (2) a hop extract material selected from the group consisting of an alpha-acid, a desoxy-alpha-acid, a hop oil, a hop wax and a mixture thereof.

5. The method of claim 4, wherein said mixture comprises 65 wt. % beta-acids.

6. The method of claim 1, and including the step of adding a surface active agent to a solution in order to solubilize said hop extract prior to treating said food or beverage product.

* * * * *